US006947142B2

(12) United States Patent
Chen et al.

(10) Patent No.: US 6,947,142 B2
(45) Date of Patent: Sep. 20, 2005

(54) COLOR DETECTION IN RANDOM ARRAY OF MICROSPHERES

(75) Inventors: Samuel Chen, Penfield, NY (US); Krishnan Chari, Fairport, NY (US); Martin C. Kaplan, Rochester, NY (US); Douglas L. Vizard, Durham, CT (US); Joaquin Calcines, West Henrietta, NY (US)

(73) Assignee: Eastman Kodak Company, Rochester, NY (US)

( * ) Notice: Subject to any disclaimer, the term of this patent is extended or adjusted under 35 U.S.C. 154(b) by 181 days.

(21) Appl. No.: 10/606,621

(22) Filed: Jun. 26, 2003

(65) Prior Publication Data

US 2004/0263848 A1 Dec. 30, 2004

(51) Int. Cl.$^7$ ................................................ G01J 3/46

(52) U.S. Cl. ............................ 356/402; 205/226; 435/6

(58) Field of Search .................. 356/402, 71; 250/226; 435/6

(56) References Cited

U.S. PATENT DOCUMENTS

| | | | |
|---|---|---|---|
| 5,412,087 A | 5/1995 | McGall et al. | |
| 5,489,678 A | 2/1996 | Fodor et al. | |
| 5,981,180 A | 11/1999 | Chandler et al. | |
| 6,023,540 A | 2/2000 | Walt et al. | |
| 2003/0143542 A1 * | 7/2003 | Qiao et al. ...................... | 435/6 |
| 2003/0162178 A1 * | 8/2003 | O'Hagan ....................... | 435/6 |

OTHER PUBLICATIONS

Principles of Instrumental Analysis, Fourth Edition, Douglas A. Skoog, James J. Leary—An Introduction to Molecular Ultraviolet/Visible and Near–Infrared Absorption Spectroscopy, pp 123–127.

Understanding The Light Microscope, D.J. Goldstein, 1999, text book, ISBN:0–12–288660–7 (Table of contents only).

Fundamentals of Light Microscopy and Electronic Imaging, Douglas B. Murphy, 2001, text book, ISNB:0–471–25391–X (Table of contents only).

Quantum–dot–tagged microbeads for multiplexed optical coding of biomolecules, Mingyong Han, Xiaohu Gao, Jack Z. Su, Shuming Nie, Nature Biotechnology, vol. 19, pp 631–635, 2001.

Block Copolymer Lithography: Periodic Arrays of ~10 Holes in 1 Square Centimeter, Miri Park, Christopher Harrison, Paul M. Chaikin, Richard A. Register, Douglas H. Adamson, Science, vol. 276, 1997, pp 1401–1404.

Multi–analyte immunoassay, Roger P. Ekins, Journal of Pharmaceutical & Biomedical Analysis, vol. 7, pp 155–168, 1989.

Cross–Reactive Chemical Sensor Arrays, Chem. Rev., 2000, 100, 2595–2626, Keith J. Albert, Nathan S. Lewis, Caroline L. Schauer, Gregory A. Sotzing, Shannon E. Stitzel, Thomas P. Vaid, David R. Walt.

* cited by examiner

*Primary Examiner*—F. L. Evans
(74) *Attorney, Agent, or Firm*—William F. Noval

(57) ABSTRACT

A method of determining one or more color characteristics of a colored microsphere comprising: providing a microarray of microspheres, at least one of which has a color characteristic; capturing the microarray with an electronic color image sensor assembly having a matrix of pixels to produce an electronic microarray image; detecting the location of a microsphere within the captured microarray image; and identifying a color characteristic of the detected microsphere.

13 Claims, 2 Drawing Sheets

COLOR DETECTION IN RANDOM ARRAY OF MICROSPHERES

FIELD OF THE INVENTION

This invention relates in general to microarray sensing technology. In particular, it concerns color and color level detection in a microarray coated on a substrate that contain no designated sites prior to coating.

BACKGROUND OF THE INVENTION

The concept of multi-analyte sensing using array based sensors (Chem. Rev. 100, 2595–2626, (2000)) has opened up a wide field of technologies in detecting and analyzing specific components (analytes) in a mixture of unknowns. Such technologies benefit industries ranging across the medical, biological, environmental, and consumer sectors. For example, the medical industry depends on analysis for the detection of metabolites, drugs, and glucose; the biological sector needs to detect amino acids, cell components; environmentalists have a need to know the level of gaseous components in water or air; while consumers may want to regularly test for levels of carbon monoxide in houses, airborne allergens, or hardness of water.

The basic principles of microarray assays were already described by the end of the eighties (J. Pharm Biomed Anal 7, 155–168, (1989)). Interest increased dramatically with the development of DNA chip technology. The invention and demonstration in the early 1990s (Science, 251, 767–773, (1991)) of high-density arrays formed by spatially addressable deposition of sensors on a two-dimensional solid support has enhanced and simplified the process of array based sensor technologies. The key to current microarray technology is the placement of receptors at predetermined locations on a microchip in a "spatially addressable" manner. The presence or absence of an analyte is then discerned by monitoring a specific location on a sensor array of receptors. All of these systems require preparing a sensor array with a plurality of receptors at predetermined sites that involve complex and expensive processing steps.

Recent technologies have used various approaches to fabricate microarrays. For example, U.S. Pat. Nos. 5,412,087, and 5,489,678 demonstrate the use of a photolithographic process for making peptide and DNA microarrays. These patents teach the use of photolabile protecting groups to prepare peptide and DNA microarrays through successive cycles of deprotecting a defined spot on a 1 cm×1 cm chip by photolithography, then flooding the entire surface with an activated amino acid or DNA base. Repetition of this process allows construction of a peptide or DNA microarray with thousands of arbitrarily different peptides or oligonucleotide sequences at different spots on the array. This method is expensive. Park et al. (Science 276:1401 (1997)) have disclosed a lithographic method for producing an array of nanometer-sized holes using polystyrene-polybutadiene copolymer masks in reactive ion etching of silica nitride. This multi-step method is capable of producing arrays of picoliter-sized holes that are typically 20 nanometers in diameter and 20 nanometers deep with a spacing of 40 nanometers. Hole densities of up to $10^{11}$ holes/cm$^2$ are disclosed. The range of sizes and spacings of the holes produced by this method is limited by the size of the copolymer microdomains. Uniformity of hole size and spacing is difficult to maintain with this method due to difficulties in controlling the etching method employed to form the holes.

Because the number of bioactive probes to be placed on a single chip usually runs anywhere from 1,000 to 100,000 probes, the spatially addressable method is intrinsically expensive regardless of how the chip is manufactured. An alternative approach is the use of fluorescent dye-incorporated polymeric beads to produce biological multiplexed arrays. U.S. Pat. No. 5,981,180 discloses a method of using color coded beads in conjunction with flow cytometry to perform multiplexed biological assay. Microspheres conjugated with DNA or monoclonal antibody probes on their surfaces were dyed internally with various ratios of two distinct fluorescence dyes. Hundreds of "spectrally addressable" microspheres were allowed to react with a biological sample and the "liquid array" was analyzed by sequentially passing microspheres through a flow cytometry cell to decode sample information. U.S. Pat. No. 6,023,540 discloses the use of fiber-optic bundles with pre-etched microwells at the distal ends to assemble dye loaded microspheres. The surface of each spectrally addressed microsphere was attached with a unique bioactive agent and thousands of microspheres carrying different bioactive probes combined to form "beads array" on pre-etched microwells of fiber optical bundles. More recently, a novel optically encoded microsphere approach was accomplished by using different sized zinc sulfide-capped cadmium selenide nanocrystals incorporated into microspheres (Nature Biotech. 19, 631–635, (2001)). Given the narrow spectral band width demonstrated by these nanocrystals, this approach significantly expands the spectrally addressable barcoding capacity in microspheres.

Even though the "spectrally addressed microsphere" approach does provide an advantage in terms of its simplicity over the old fashioned "spatially addressable" approach in microarray making, there are still needs in the art to render the manufacture of microarrays less difficult and less expensive.

U.S. patent application Ser. No. 09/942,241 discloses a microarray that is less costly and easier to prepare than those previously disclosed, because the support need not be modified, even though the microspheres remain immobilized on the substrate. The disclosed microarray includes microspheres dispersed in a fluid containing a gelling agent or a precursor to a gelling agent, wherein the microspheres are immobilized at random positions on the substrate. The substrate is free of receptacles designed to physically or chemically interact with the microspheres. Disclosed are a unique coding composition and technology to prepare a microarray on a substrate that does not require placement of microspheres at predetermined locations. Various coating methods are taught, but there is exemplified machine coating, whereby a support is layered with a fluid coating composition comprising microspheres dispersed in gelatin. Immediately after coating, the support is passed through a chill-set chamber in the coating machine where the gelatin undergoes rapid gelation and the microspheres are immobilized.

Although the disclosure of this patent application provides a manufacturing advantage over other existing technologies, some limitations need to be overcome. By moving from spatially addressable to randomly positioned microspheres, the information content contained within each bead necessarily must be extracted using a new analysis technology that is not preset-positionally dependent. Furthermore, the colors and color levels need to be accessed uniquely to correlate the tag to the analyte.

It is also known (Nature Biotech. 19, 631–635, (2001)) that the number of different color codes in spectrally addressable microspheres for use in multi-analyte sensing follows the relationship:

Number of optical codes=$(n^m-1)$, where m=color types, and n=color intensity levels For example, 2 colors, with 4 intensity levels each should result in $4^2-1=15$ codes. Hence, in order to sense a large number of analytes using several color types and numerous color levels, there exists a need for analysis methods to differentiate small changes in color types and color levels, on a micrometer scale.

SUMMARY OF THE INVENTION

According to the present invention, there is provided a solution to the problems of the prior art.

Generally, the present invention provides a method to analyze and to determine different color types as well as different color levels in individual microspheres (beads) loaded with colorants. This method uses a combination of an optical microscope together with a multi-color sensing electronic sensor based digital camera such that a magnified image of individual microspheres is first made, and then the spectral information within each bead, or in the entire bead, is identified. Through the proper selection of optic lens to provide a desired magnification, first a digital image of the bead array is captured, so that the location of each bead can be detected. Then the center position of each bead is calculated, and a select region with similar pixel values around that pixel position is created. The number of pixels of this region is smaller than the total number of pixels in the entire imaged bead region. The pixel value in this "sub-bead" region is then processed to give an averaged pixel value. The color channel and averaged pixel value in this "sub-bead" region is then used to identify the color type and color level present in the bead.

According to a feature of the present invention there is provided a method of determining one or more color characteristics of a colored microsphere comprising: providing a microarray of microspheres, at least one of which has a color characteristic; capturing said microarray with an electronic color image sensor assembly having a matrix of pixels; detecting the location of a microsphere within said captured microarray image; and identifying a color characteristic of said detected microsphere.

ADVANTAGEOUS EFFECT OF THE INVENTION

The invention has the following advantages.

1. A method whereby randomly distributed, color addressable mixed beads in a unique composition can be processed to extract its color content in a simple, cost effective, and efficient manner.

2. A method to analyze the color content of microarrays that does not require expensive and complex spatially addressable coated microarrays, or spectrally addressable liquid microarrays.

DETAILED DESCRIPTION OF THE INVENTION

Figure 1:
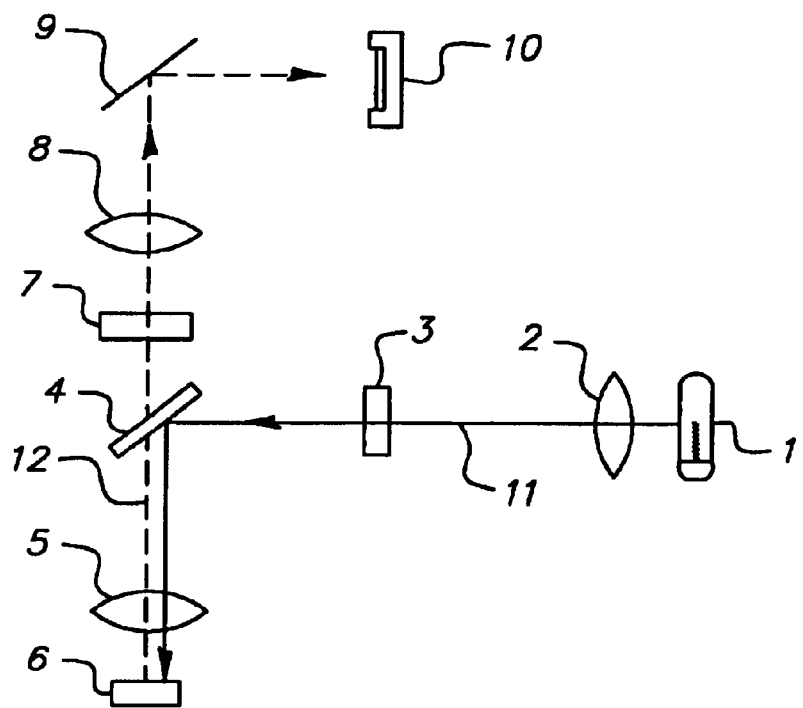
FIG. 1 is a schematic diagram showing the combination of optical microscope and digital camera, assembled together for detecting color and color levels in colored microspheres.

Color type and color level identification in microspheres is demonstrated using a hybrid analysis system including two parts: an optical microscope (or other optical imaging system) coupled to a three-color sensor (e.g., CCD, CMOS) digital camera. This system, shown in FIG. 1, uses high-intensity light, lenses, mirrors, color filters, apertures and optical detectors to first generate a magnified image of a coated array of randomly positioned microspheres. An image consists of 3 mono-colored images, each is taken using, for example, a red, green, or blue color filter and then merged to form a full color image. Such an image not only identifies the location of all the microspheres, FIG. 2, but also images the microsphere beads at sufficient resolution to allow for the subsequent color analysis process. It will be understood that other colors can be used.

The microarray of beads is preferably that of the disclosure in U.S. patent application Ser. No. 09/942,241, in which color addressable mixed beads in a unique composition are randomly distributed on a substrate that has no wells, nor sites to attract the microspheres. In the preferred embodiment, the beads are coated on a mirrored support. In a second preferred embodiment, the beads are coated on transparent support. In a third preferred embodiment, the beads are coated on a black support.Referring to FIG. 1, the procedure for obtaining a magnified image starts by focusing light excitation (solid arrow 11) from a light source, 1, (e.g. tungsten, halogen or xenon lamp), through the collector lens assembly, 2, through a spectral filter, 3, reflecting from a dichroic mirror, 4, through an objective lens, 5, and onto the microarray specimen, 6. The emitted or reflected light (dashed arrow 12) is then focused by the objective lens, 5, and passed through the dichroic mirror, 4, and filter 7 so that an image of a given field of view can be captured. Some adjustment to the overall magnification is carried out by the 1–2× power variable zoom lens, 8. The mirror, 9, directs the light to the electronic digital camera, 10, for digital image capture. In one embodiment, the optical microscope used is an Olympus BX-30MFSP modular optical system (from Olympus PID Corp, Woodbury, N.Y.), equipped with a Spot RT-Slider Color Camera (with a 1520×1080 pixel array CCD sensor from Diagnostic Instruments, Inc.). Depending on the magnification used, optical microscope imaging can provide the location of hundreds to thousands of beads in a single field of view. The combination of many images can provide the location to tens and hundreds of thousands of bead locations. This application requires capturing two images, one to determine the presence of analytes of interest, and the second to decode the color types and levels in beads tagged with the analyte. Once the color code is unraveled the identity of each analyte becomes known.

Figure 2:
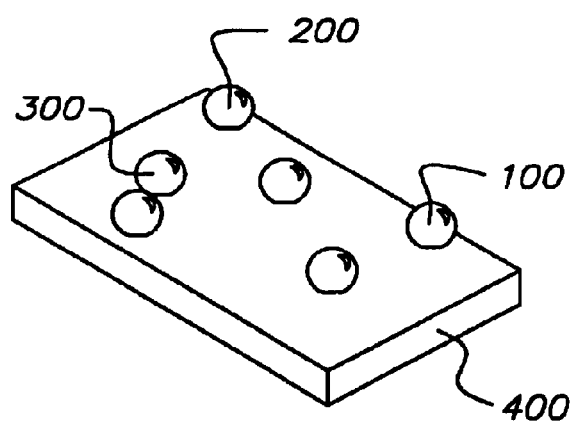
FIG. 2 is a schematic diagram showing randomly distributed microspheres containing a bead without color and two beads containing a colorant loaded at different concentration levels, all coated and immobilized on a substrate surface.

FIG. 2 shows randomly distributed microspheres 100 having no color and microspheres 200 and 300 containing a colorant loaded at different concentration levels, all coated and immobilized on a substrate 400.

The first image examines the presence of the analyte after it has been attached to the bead, and it is captured using fluorescence microscopy. Such an image identifies the location of the analyte tagged on the microsphere. This imaging technique uses various color filter cube assemblies (e.g.

U-M57, from Olympus PID Corp, Woodbury, N.Y.), each consisting of an exciter filter, 3, a dichroic mirror, 4, and a barrier filter, 7. These can be rotated or translated into the optical microscope to selectively extract the fluorescence from the analyte tagged on the microsphere. The exciter filter selects the wavelength of the incident light to cause electronic excitation of the analyte species in order to induce fluorescence, which is then channeled through the barrier filter, 7, for a fluorescence image that can be captured by the digital camera, 10. Not all microspheres are necessarily tagged with an analyte. The fluorescence image identifies the presence and location of the analyte in a given field of view.

A second full-color image (either bright field or dark field) from the same field of view is then captured by translating out the fluorescence filter assembly, but without disrupting the viewing or image capturing process. This image reveals the locations and colors of all the microspheres in the field of view. It is formed by sequentially taking three color images, each using a red, green or blue color filter, and then merging the three images into a full-color digital image. These pairs of images not only define the presence of the analyte, but also provide the location relationship between the tagged analyte and the color-coded microspheres. Optical microscopy and fluorescence microscopy methods are broadly described by D. B. Murphy, "Fundamentals of Light Microscopy and Electronic Imaging", Wiley-Liss, Inc. Publishing, (2001); and D. J. Goldstein, "Understanding the Light Microscope. A Computer-aided Introduction", Academic Press, California, (1999).

The location of each bead, or at least each bead that fluoresced, is determined either manually or by image processing software. Manual determination is carried out by a person observing the image, recognizing the location of the bead, and specifying the location, such as by reporting the coordinates or pointing to the bead with a computer pointing device such as a mouse. Alternatively, fully automated (no human intervention) location of each bead may be performed by any of numerous, well know computer image processing algorithms, such as template matching, segmentation, thresholding and region growing, or cluster analysis.

If the color analysis is being performed on full beads, rather than sub-regions of the beads, lower image magnification (or even demagnification) is sometimes sufficient, with the image resolution being much coarser than the diameter of a bead. With such magnification, and sparsely coated, non-aggregated (isolated) beads, most beads fall entirely within a single pixel. Finding the locations of beads is simpler in this case, involving image processing to find pixels that differ from background, such as thresholding. No region growing or other segmentation image processing is necessary, if the analysis discards the rare instance where a bead straddles the boundary between pixels. At such low resolution, dark-field imaging has the advantage that the background (the dark-field) contributes little to the image signal, minimizing contamination of the signal from the colored beads.

Figure 3:
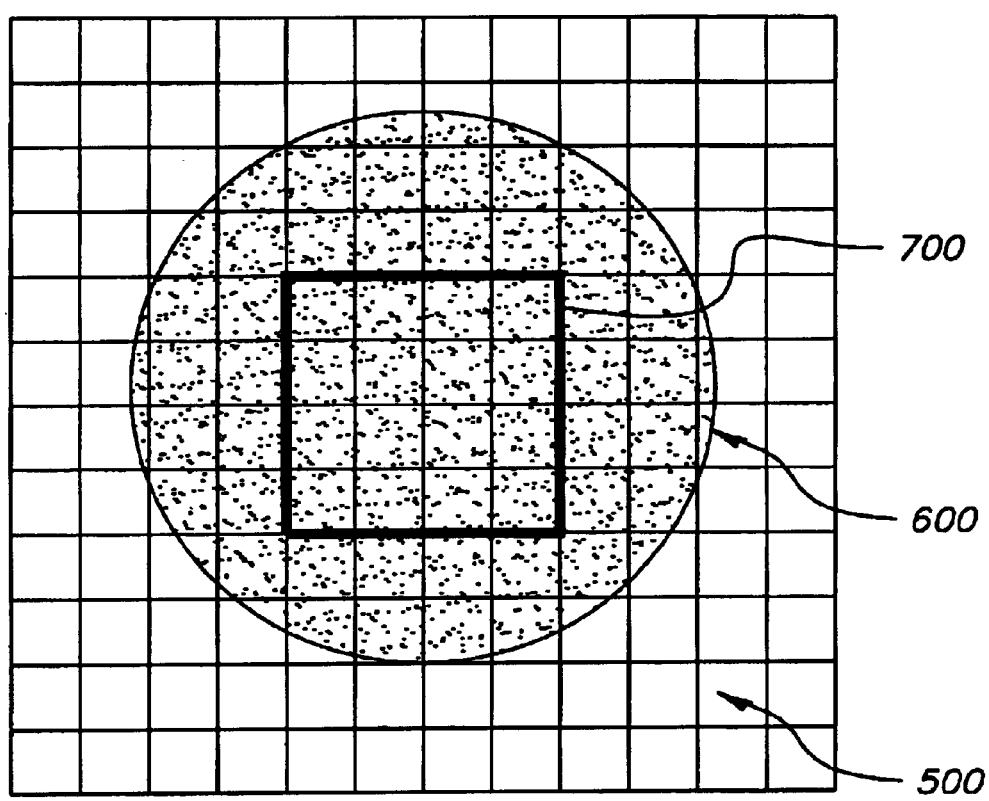
FIG. 3 is a diagrammatic view of a digital image of a colored optical bead.

At higher magnifications, it is possible to determine the color of each bead by examining its primary color content in a sub-bead region of the imaged microsphere. A sub-bead region, and not the entire bead region, is used for color processing primarily to bypass imaging artifacts introduced by the shape of the microspheres. Referring to FIG. 3, there is shown the pixel array in a digital image 500, the colored microsphere 600 and the sub-bead region 700 of the microsphere 600. Due to its spherical or near-spherical shape, light traveling through the bead undergoes a "focusing" effect, as light is bent to varying degrees depending which part of the bead is traversed. This results in non-uniformity in spectral information displayed in different parts of the bead image. Usually the bead images take on a morphology with a darker band on its periphery. This region can take on different color, intensity, or hue when compared to the central region. Other imaging artifacts, such as chromatic aberration, may also be present and can also contribute to non-uniformity between the periphery and the central region of the imaged bead. In order to extract the color type and color level information, non-obvious procedures need to be taken to reduce or exclude this non-uniformity when calculating the representative color of the bead. Our method of sub-bead spectral analysis deliberately excludes the outer region of the imaged bead, and uses an image processing method to evaluate only the pixel values in the central region of the imaged bead.

While details of how to exclude the type of imaging artifacts described here may be different from one process to another, the overall method of sub-bead analysis usually follows one of two approaches. Either the periphery is actively selected and then excluded, so that the default central region can be analyzed; or the central region is actively selected and used, thereby indirectly exclude the periphery. In the preferred embodiment, the latter method is preferable, and image processing of the bead color used Photoshop 6.0 (Adobe Systems Inc., San Jose, Calif.) and the various image manipulation tools contained within. This package is relatively inexpensive, readily accessible by most users, and contains the essentials of the image processing tools for sub-bead analysis.

Once the location of the bead is known, the center pixel position 700 is then calculated. This pixel position can be selected by the Magic Wand tool, set with an appropriate Tolerance range. This tool effectively creates a "sub-bead" region approximately centered around the selected center pixel position, such that this smaller region contains pixels whose values are within the tolerance range of that in the central pixel. The averaged pixel values from this selected region can then be calculated for each of the primary color channels (red, green or blue) using the histogram algorithm of Photoshop 6.0. Since each image is a composite of the red, green and blue channels, the individual pixel value in each primary color channel is readily accessible for such calculations. Finally, by comparing the averaged pixel values in the sub-bead region to a look up table of known values for either the pure colors, or a mixture of colors, the identity of the colorant (from the color channels) and the colorant levels in the bead (from the averaged pixel value of the sub-bead region) can then be assigned.

In this analysis, it is pointed out that the pixel resolution of the image, relative to the imaged bead size is of importance. Preferably, for sub-bead analysis, the area of each pixel is less than one ninth the cross-sectional area of a typical bead. This allows for at least one central pixel to be selected that is representative of its central region.

EXAMPLE 1

This example illustrates the analysis method to detect different levels of magenta colorant and yellow colorant in microspheres loaded with two different levels of magenta and yellow colorants respectively.

Preparation of Plain (Non-Dyed) Beads

A. 4.2% aqueous suspension of polystyrene beads prepared by emulsion polymerization and having a mean size of 10 micrometers was obtained from Interfacial Dynamics Corporation, Portland, Oreg.

B. Preparation of Magenta Colored Beads M1

A suspension of magenta colored beads M1 was prepared by first dissolving 0.001 gram of Dye 2 in 0.02 grams of toluene and 5 grams of acetone. 5.0 grams of the suspension of non-dyed beads from part A was combined with 3 grams of acetone. This mixture was then added rapidly to 2 grams of the solution of Dye 2 in acetone and toluene while stirring to prepare a suspension of colored beads. The suspension of colored beads was then filtered using a porous cotton filter, poured into a dialysis bag (12,000 to 14,000 molecular weight cut off) and washed with distilled water for one hour. After washing, the suspension of colored beads was filtered again using a porous cotton filter.

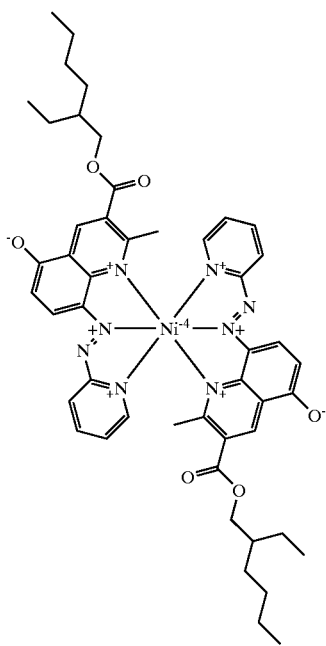

Dye 2

C. Preparation of Magenta Colored Beads M2

A suspension of magenta colored beads M2 was prepared by first dissolving 0.0015 grams of Dye 2 in 0.02 grams of toluene and 2 grams of acetone. 5.0 grams of the suspension of non-dyed beads from part A was combined with 3 grams of acetone. This mixture was then added rapidly to the solution of Dye 2 in acetone and toluene while stirring to prepare a suspension of colored beads. The suspension of colored beads was then filtered using a porous cotton filter, poured into a dialysis bag (12,000 to 14,000 molecular weight cut off) and washed with distilled water for one hour. After washing, the suspension of colored beads was filtered again using a porous cotton filter.

D. Preparation of Yellow Colored Beads Y1

A suspension of yellow colored beads Y1 was prepared by first dissolving 0.004 grams of Dye 1 in 0.02 grams of toluene and 2 grams of acetone. 5 grams of the suspension of non-dyed beads from part A was combined with 3 grams of acetone. This mixture was then added rapidly to the solution of Dye 1 in acetone and toluene while stirring to prepare a suspension of colored beads. The suspension of colored beads was then filtered using a porous cotton filter, poured into a dialysis bag (12,000 to 14,000 molecular weight cut off) and washed with distilled water for one hour. After washing, the suspension of colored beads was filtered again using a porous cotton filter.

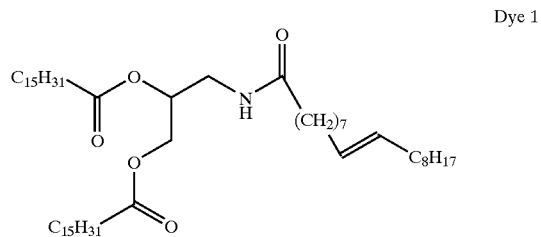

Dye 1

E. Preparation of Yellow Colored Beads Y2

Same as preparation of yellow colored beads Y1 except that the amount of dye used was 0.008 grams instead of 0.004 grams.

F. Preparation of Coated Array containing Dyed Beads M1, M2, Y1 and Y2 and Non-Dyed Beads One hundred micro-liters of a 3% aqueous solution of Type IV gelatin was spread on a metallized plastic support (comprising a micron thick layer of evaporated aluminum on polyethyleneterephthalate (PET)) at 40 C using a coating knife (0.1 mm gap). The gelatin layer was then allowed to dry.

After the gelatin layer had dried, 0.02 grams of the suspension of yellow colored beads Y1 was combined with 0.02 grams of yellow colored beads Y2, 0.02 grams of magenta colored beads M1, 0.02 grams of magenta colored beads M2 and 0.02 grams of a suspension of non-dyed (plain) beads (4.2% solids) and diluted with 8 mL of water. Fifty micro-liters of this combination were then coated onto the gelatin layer that was maintained at a temperature of 12 C. The coating was then allowed to dry at 12 C.

G. Color and Color Level Processing of Dyed Microspheres.

The coating was imaged with a 10× objective lens (Olympus UplanApo, 0.40 NA), using a Spot RT Slider camera. In the image each bead was resolved by approximately 35×35 array of pixels. When processed in Photoshop 6.0, the Magic Wand was set with a tolerance range of 25, and the green channel was monitored. Of the 10 light magenta beads, and 10 dark magenta beads selected at random, the average pixel values of the central sub-bead region for each is shown in Table 1.

TABLE 1

Image processed Pixel Value of Magenta Colored Beads (Magic Wand, range = 25, taken on bead center)

| | Dark Magenta Green Channel CV | Light Magenta Green Channel CV |
|---|---|---|
| 1 | 102 ± 8 | 162 ± 7 |
| 2 | 105 ± 7 | 151 ± 11 |
| 3 | 111 ± 6 | 143 ± 9 |
| 4 | 95 ± 8 | 144 ± 8 |
| 5 | 109 ± 8 | 144 ± 9 |
| 6 | 111 ± 10 | 126 ± 10 |
| 7 | 104 ± 8 | 146 ± 8 |
| 8 | 101 ± 6 | 130 ± 10 |
| 9 | 103 ± 8 | 157 ± 8 |
| 10 | 108 ± 7 | 152 ± 9 |
| Avg | 105 | 145 |

An average of these averaged pixel values (with a range of ±20 units) clearly shows that there is a statistical difference in pixel value in the sub bead region to differentiate a dark magenta (145±20) from a light magenta (105±20) bead.

Of the 10 light colored yellow beads, and 10 dark yellow beads selected at random, the average pixel values of the central sub-bead region for each is shown in Table 1.

TABLE 2

Image processed Pixel Value of Yellow Colored Beads
(Magic Wand, range = 25, taken on bead center)

|  | Dark Yellow<br>Blue channel | Light Yellow<br>Blue Channel |
|---|---|---|
| 1 | 79 ± 7 | 141 ± 5 |
| 2 | 99 ± 5 | 138 ± 4 |
| 3 | 90 ± 5 | 141 ± 4 |
| 4 | 98 ± 6 | 148 ± 3 |
| 5 | 99 ± 7 | 146 ± 3 |
| 6 | 77 ± 6 | 138 ± 9 |
| 7 | 79 ± 5 | 133 ± 10 |
| 8 | 79 ± 7 | 160 ± 5 |
| 9 | 88 ± 5 | 142 ± 8 |
| 10 | 78 ± 6 | 139 ± 9 |
| Avg | 86 | 143 |

An average of these averaged pixel values (with a range of ±20 units) clearly shows that there is a detectable difference in pixel value in the sub bead region to differentiate a dark yellow (143±20) from a light yellow (86±20) bead.

While the preferred embodiment uses a 3-color camera system (red, green, blue), other embodiments include different numbers of color channels (e.g. 4-channel) and other spectral channels (e.g. infrared, red, green instead of red, green, blue).

In another embodiment, the aforementioned fluorescence signal is replaced by a chemiluminescent signal, in which the chemical reaction of the analyte with a bead generates emitted light without need for a stimulating light beam.

Other algorithms for selecting the pixels representing a bead's color are within the spirit of the invention. In one such embodiment, all pixels within a certain distance of the center of the bead are chosen (e.g. within 0.5 of the bead radius), rather than using the Photoshop Magic Wand to select pixels. In yet another embodiment, lower magnification (or demagnification) is used, with a pixel size larger than a bead, and each bead represented by a single such large pixel (except for the occassional bead that straddles the border between two pixels).

The invention has been described in detail with particular reference to certain preferred embodiments thereof, but it will be understood that variations and modifications can be effected within the spirit and scope of the invention.

Parts List 1 light source
2 collector lens assembly
3 spectral filter
4 dichroic mirror
5 objective lens
6 microarray specimen
7 filter
8 2× power variable zoom lens
9 mirror
10 electronic digital camera
11 illumination light beam
12 emitted or reflected light beam
100 distributed microspheres
200 distributed microspheres
300 distributed microspheres
400 substrate
500 digital image
600 colored microsphere
700 sub-bead region

What is claimed is:

1. A method of determining one or more color characteristics of a colored microsphere comprising:

providing a microarray of microspheres, at least one of which has a color characteristic;

capturing said microarray with an electronic color image sensor assembly having a matrix of pixels to produce an electronic microarray image;

detecting the location of a microsphere within said electronic microarray image; and identifying a color characteristic of said detected microsphere.

2. The method of claim 1 wherein said providing provides a microarray of randomly distributed microspheres.

3. The method of claim 2 wherein said microarray includes a coating of a plurality of microspheres on a substrate that has no walls nor sites to attract the microspheres.

4. The method of claim 1 wherein in said capturing said electronic color image sensor assembly includes red, green and blue sensors which capture red, green and blue images which are merged to form a full color microarray image.

5. The method of claim 1 wherein a microsphere in said microarray image falls within the area of a single pixel.

6. The method of claim 1 wherein a microsphere in said microarray image falls within a plurality of pixels and wherein said identifying identifies a color characteristic of said detected microsphere from a subset of pixels of said plurality of pixels.

7. The method of claim 6 wherein said subset of pixels is centrally located within said plurality of pixels.

8. The method of claim 1 wherein said capturing captures a magnified image of said microarray and each microsphere is captured by a plurality of pixels; and wherein said identifying includes identifying said color characteristic of said detected microsphere from a subregion of the image of said detected microsphere, said subregion being a subset of pixels of said plurality of pixels.

9. The method of claim 8 wherein said subset of pixels is centrally located within said plurality of pixels.

10. The method of claim 8 wherein said captured magnified image is produced by optical magnification.

11. The method of claim 1 wherein in said capturing said electronic color image sensor assembly includes a monochrome sensor and red, green and blue filters which sequentially capture red, green and blue images which are merged to form a full color microarray image.

12. The method of claim 1 wherein in said capturing said electronic color image sensor assembly includes sensors having at least two different spectral responses which capture at least two different spectral images which are merged to form a color or pseudo-color microarray image.

13. The method of claim 1 wherein in said capturing said electronic color image sensor assembly includes a monochrome sensor and at least two different spectral filters which sequentially capture at least two different spectral images images which are merged to form a color or pseudo-color microarray image.

* * * * *